United States Patent [19]

Fischer et al.

[11] Patent Number: 4,853,473
[45] Date of Patent: Aug. 1, 1989

[54] PREPARATION OF 2(5H)-FURANONES

[75] Inventors: Rolf Fischer, Heidelberg; Juergen Frank, Schwetzingen; Franz Merger, Frankenthal; Michael Roeper, Wachenheim; Uwe Vagt, Speyer, all of Fed. Rep. of Germany

[73] Assignee: BASF Aktiengesellschaft, Ludwigshafen, Fed. Rep. of Germany

[21] Appl. No.: 201,050

[22] Filed: Jun. 1, 1988

[30] Foreign Application Priority Data

Jun. 3, 1987 [DE] Fed. Rep. of Germany ....... 3718527

[51] Int. Cl.$^4$ ............................................. C07D 307/88
[52] U.S. Cl. ...................................................... 549/326
[58] Field of Search ........................................ 549/326

[56] References Cited

U.S. PATENT DOCUMENTS

| | | | |
|---|---|---|---|
| 2,809,203 | 10/1957 | Leonard | 549/326 |
| 4,324,727 | 4/1982 | Merger et al. | 549/326 |
| 4,360,692 | 11/1982 | Kummer et al. | 560/175 |
| 4,420,622 | 12/1983 | vande Moesdijk et al. | 549/326 |

FOREIGN PATENT DOCUMENTS 31199 1/1981 European Pat. Off. .
3506632 8/1986 Fed. Rep. of Germany .

OTHER PUBLICATIONS

Armengaud, Academie Des Sciences, 5-21-62, pp. 3696-3698.

A. Cowell and J. K. Stille, Tetrahedron Letters (1979), p. 133.
Can. J. Chem. 58 (1980), p. 2484.
C. J. Cavallito and T. H. Haskell, J. Am. Chem. Soc. 68 (1946), p. 2332.
S. Inayama and T. Kawamata, Chem. Pharm. Bull. (1973), p. 461.

Primary Examiner—Richard L. Raymond
Attorney, Agent, or Firm—John H. Shurtleff

[57] ABSTRACT

2(5H)-furanones I

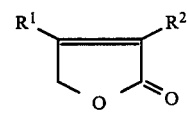
(I)

where $R^1$ and $R^2$ are each hydrogen, $C_1$–$C_6$-alkyl, $C_5$- or $C_6$-cycloalkyl, $C_7$–$C_{12}$-aralkyl or aryl, are prepared by heating a 3-formylcarboxylate or 3-formylcarboxylic acid II

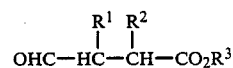
(II)

where $R^3$ is hydrogen, $C_1$–$C_{12}$-alkyl, $C_5$- or $C_6$-cycloalkyl, $C_7$–$C_{12}$-aralkyl or aryl, to 100°–450° C. in the presence of an acidic catalyst.

14 Claims, No Drawings

PREPARATION OF 2(5H)-FURANONES

The present invention relates to a process for the preparation of 2(5H)-furanones by cyclization of 3-formylcarboxylates or 3-formylcarboxylic acids.

It is known that 3-methyl-2(5H)-furanone (3-methyl-2,5-dihydrofuran-2-one) can be prepared, for example, starting from 1-hydroxy-3-oxobutane (Ch. J. Cavallito and Th. H. Haskell, J. Am. Chem. Soc. 68 (1946), 2332), 2-methyl-3-butenecarboxylic acid (M. Franck-Neumann and Ch. Berger, Bull. Soc. Chim. France 1968, 4067), 3-methylbutyrolactone (S. Inayama and T. Kawamata, Chem. Pharm. Bull. 1973, 461) or 2-butyn-1-ol (A. Cowell and J. K. Stille, Tetrahedron Lett. 1979, 133).

4-Methyl-2(5H)-furanone is obtainable, for example, by hydrogenation of methylmaleic anhydride with a metal hydride (Can. J. Chem. 58 (1980), 2484).

The stated synthesis routes are unsatisfactory since they either involve numerous stages or employ starting materials which are difficult to obtain.

It is an object of the present invention to make it possible to obtain unsubstituted or substituted 2(5H)-furanones by a simple method.

We have found that this object is achieved by a process for the preparation of 2(5H)-furanones of the general formula I

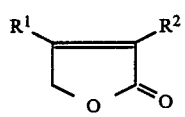

where $R^1$ and $R^2$ are each hydrogen, $C_1$–$C_6$-alkyl, $C_5$- or $C_6$-cycloalkyl, $C_7$–$C_{12}$-aralkyl or aryl, wherein a 3-formylcarboxylate or 3-formylcarboxylic acid of the general formula II

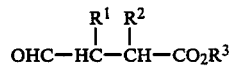

where $R^3$ is hydrogen or $C_1$–$C_{12}$-alkyl, $C_5$- or $C_6$-cycloalkyl, $C_7$–$C_{12}$-aralkyl or aryl, is heated to 100°–450° C. in the presence of an acidic catalyst.

For the preparation of 4-ethyl-2(5H)-furanone from methyl 3-formylvalerate, the reaction according to the invention can be represented by the following equation:

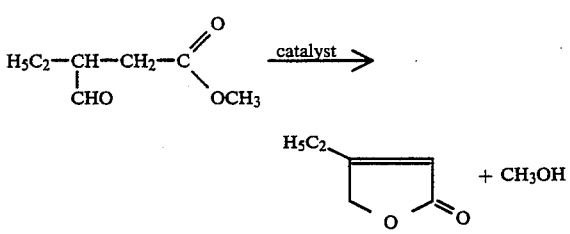

Suitable acidic catalysts are catalysts dissolved to give homogeneous solutions or, in particular, heterogeneous catalysts, for example catalyst suspended in the reaction mixture. For example, mineral acids, such as sulfuric acid, phosphoric acid, hydrochloric acid, nitric acid or hydrogen bromide, or sulfonic acids, such as benzenesulfonic acid or p-toluenesulfonic acid, are suitable. Acidic ion exchangers in their H form, which are composed, for example, of crosslinked polystyrene containing sulfo groups, may also be used.

Preferred catalysts are acidic oxides of elements of main groups III and IV and of subgroups IV to VI of the Periodic Table. Examples are silica, for example in the form of silica gel, kieselguhr or quartz, boron trioxide, aluminum trioxide, titanium dioxide, zirconium dioxide, vanadium pentoxide and oxides of chromium, of molybdenum or of tungsten, as well as mixtures of these oxides.

Other preferred catalysts are silicate materials having a large surface area, such as natural or synthetic zeolites. Such zeolites are mentioned, for example, in C. K. Hersh, Molecular Sieves, Reinhold Publishing Company, New York (1961), page 21, Table 3-1, or in Ullmanns Enzyklopädie der technischen Chemie, 4th Edition, Volume 17, pages 9–16, and Volume 24, pages 575–577. Particularly suitable zeolites are those of the chabasite and mordenite groups and especially those of the faujasite and pentasil groups. Advantageous synthetic zeolites are those having a pronounced zeolite framework with a high silica content, such as X and Y zeolites and pentasil zeolites, eg. aluminosilicate, borosilicate and iron silicate zeolites of the pentasil type, which may be doped with transition metals, for example with noble metals, such as Pd, rare earth metals, such as Ce or La, or with iron, zinc or tungsten. Such pentasil zeolites and their preparation are described in, for example, German Laid-Open Application DOS No. 3,506,632.

Suitable starting materials II are 3-formylcarboxylic acids and their esters. Since, in the preparation of these starting compounds, the esters are frequently obtained, for example in the hydroformylation of pentenoates or acrylates (cf. EP-A-31 100 or J. Falbe and N. Huppes, Brennstoffchemie, 48 (1967), 46–52), it may be advantageous to use the esters directly for the reaction according to the invention.

Suitable radicals $R^1$ and $R^2$ in the starting materials II are hydrogen, $C_1$–$C_8$-alkyl, in particular branched or straight-chain $C_1$–$C_4$-alkyl, $C_5$- or $C_6$-cycloalkyl, $C_7$–$C_{12}$-aralkyl or aryl. Alkyl and cycloalkyl are, for example, methyl, ethyl, propyl, isopropyl, butyl, sec-butyl, tert-butyl, cyclopentyl or cyclohexyl. Aralkyl and aryl are, for example, benzyl, phenylethyl, phenyl, tolyl, xylyl or naphthyl, and the aromatic nucleii may each carry groups which are inert under the reaction conditions, such as $C_1$–$C_4$-alkyl, $C_1$–$C_4$-alkoxy, halogen, eg. fluorine, bromine or chlorine, or $C_1$–$C_4$-haloalkyl. $R^1$ and $R^2$ are each particularly preferably hydrogen or alkyl.

$R^3$ may be varied very widely and is hydrogen, $C_1$–$C_{12}$-alkyl, $C_5$- or $C_6$-cycloalkyl, $C_7$–$C_{12}$-aralkyl, such as phenylethyl or benzyl, or aryl, eg. unsubstituted or substituted phenyl. Advantageously, $R^3$ is chosen so that the resulting alcohol can be readily removed from the reaction mixture, for example by distillation. Low molecular weight alkyl radicals of 1 to 6 carbon atoms, cyclohexyl, cyclopentyl, phenyl and benzyl are advantageous.

Examples of suitable starting compounds II are 3-formylbutyric acid, 3-formylvaleric acid, 3-formylpropionic acid, 2-methyl-3-formylpropionic acid, in particular in the form of their methyl, ethyl, propyl, butyl, cyclohexyl, phenyl and benzyl esters.

The reaction of the 3-formylcarboxylates can be carried out continuously or batchwise in the liquid phase or in the gas phase under atmospheric or superatmospheric pressure, advantageously under from 1 to 50, in particular from 1 to 5, bar. The reaction temperature is from 100° to 450° C., in particular from 200° to 350° C.

The reaction in the liquid phase is carried out, for example, by heating to the desired reaction temperature in the presence of a suspended fixed-bed catalyst or of a homogeneously dissolved catalyst. The amount of catalyst in the case of a homogeneous solution of a mineral or sulfonic acid may be from 0.002 to 0.25 mole per mole of starting material II. In the case of heterogeneous, suspended catalysts, it is in general from 0.5 to 20% by weight, based on the starting material II, of catalyst.

Working up may be carried out in a conventional manner by removing the catalyst, for example by filtration or neutralization, and subjecting the reaction mixture to fractional distillation to obtain the lactones I.

In the case of reactions in the gas phase, which are frequently preferred, an advantageous procedure comprises initially vaporizing the starting material II and then passing it in gaseous form, if necessary together with an inert gas, such as nitrogen, carbon dioxide or argon, at the desired reaction temperature over a fixed-bed or fluidized catalyst. The space velocity may advantageously be from 0.1 to 10, in particular from 0.1 to 5, g of II per g of catalyst per hour. The reacted mixture can be condensed by means of a suitable cooling apparatus and then worked up in a conventional manner by fractional distillation. Unconverted formyl esters II can be recycled to the synthesis stage.

With regard to the selectivity and catalyst life in the novel reaction, it may be advantageous to carry out the reaction in the presence of a solvent. Suitable solvents are water, alcohols, such as methanol, ethanol, propanol, isopropanol or butanols, hydrocarbons, such as pentane, hexane or petroleum ether, halohydrocarbons, such as methylene chloride, chloroform or 1,2-dichloroethane, and ethers, such as methyl tert-butyl ether, dioxane or tetrahydrofuran, as well as mixtures of these solvents. Preferred solvents are water and/or $C_1$–$C_4$-alcohols.

The molar ratio of formylcarboxylate II to solvent may be, for example, from 1:0.1 to 1:50, in particular from 1:0.5 to 1:20.

The 2(5H)-furanones I which can be prepared by the novel process are useful intermediates, for example for the preparation of herbicides (French Pat. No. 2,475,547) and $C_5$-phosphorylides for Wittig reactions (Aust. J. Chem. 1974, 1491–1503).

The Examples which follow illustrate the process according to the invention.

EXAMPLE 1

10 g/hour of methyl 3-formylvalerate were pumped under atmospheric pressure into an evaporator and passed from there in gaseous form, together with 3 l/hour of nitrogen, at 350° C., over 5 g of an $SiO_2$ catalyst. The catalyst was present in a coiled tube (VAA, 1 m length, 6 mm diameter) which was kept at a constant temperature of 350° C. in a hot air oven. The gaseous reacted mixture was condensed, weighed, and analysed by gas chromatography.

In a reaction time of 8 hours, 77 g of reaction product were obtained. Analysis by gas chromatography (% by area) showed that 80% of 4-ethyl-2(5H)-furanone, 9% of methyl 3-formylvalerate and 11% of unknown products were obtained. 46.7 g (75% of theory) of 4-ethyl-2(5H)-furanone of boiling point 77°–78° C./0.35 mbar and 6.5 g (8% of theory) of unconverted methyl 3-formylvalerate of boiling point 38°–40° C./0.3 mbar were obtained from the said reaction product by fractional distillation.

EXAMPLES 2 TO 7

The reactions listed in the Table below were carried out similarly to Example 1.

TABLE

Reaction of methyl 3-formylcarboxylates $$\text{OHC}-\underset{\underset{\text{II}}{|}}{\overset{\overset{R^1}{|}}{\text{CH}}}-\underset{\underset{}{|}}{\overset{\overset{R^2}{|}}{\text{CH}}}-\text{CO}_2\text{CH}_3 \longrightarrow \underset{\text{I}}{\text{[furanone]}} + \text{CH}_3\text{OH}$$

| Example | $R^1$ | $R^2$ | Catalyst | Amount of catalyst (g) | Temperature (°C.) | Reaction time (h) | End product I (%) | Educt (%) | Others (%) |
|---|---|---|---|---|---|---|---|---|---|
| 2 | H | $CH_3$ | $SiO_2$ | 5 | 400 | 3.5 | 49 | 51 | — |
| 3 | $C_2H_5$ | H | $TiO_2$ | 5 | 350 | 3 | 67 | 26 | 7 |
| 4 | $C_2H_5$ | H | $\gamma$-$Al_2O_3$ | 5 | 300 | 1 | 69 | 19 | 12 |
| 5[b] | $CH_3$ | H | $\gamma$-zeolite[c] | 5 | 350 | 2 | 72 | 21 | 7 |
| 6[b] | H | H | — | 5 | 400 | 2 | 15 | 76 | 9 |
| 7 | H | $CH_3$ | $\gamma$-zeolite | 5 | 400 | 2 | 64 | 26 | 10 |

[a]Analysis by gas chromatography, results in % by area
[b]11 g of starting material per hour
[c]0.1–1 mm chips

COMPARATIVE EXAMPLE

The reaction was carried out as described in Example 7 but using methyl levulate (methyl 4-ketopentanoate) instead of methyl 4-formylpropionate. Analysis by gas chromatography showed that, after a reaction time of 2 hours, 14% of 5-methyl-2(3H)-furanone had formed in addition to 46% of unconverted levulate. 5-Methyl-2(5H)-furanone was not obtained.

The zeolite used in the Examples was a Y zeolite which had been converted into the H form in a known manner by subjecting the commercial Na form to ion exchange with aqueous ammonium nitrate solution.

EXAMPLE 8

About 10 g/hour of 3-formylvaleric acid were pumped into an evaporator and passed from there in gaseous form, together with 3 l/hour of nitrogen, at 350° C., over 5 g of $SiO_2$ catalyst.

After a reaction time of 4 hours, the mixture was equilibrated for 2 hours. In this period, 20.7 g of 3-formylvaleric acid were fed in and 20.1 g of reacted mixture collected. 15.5 g (86% of theory) of 4-ethyl-2(5H)-furanone were obtained from this mixture by fractional distillation.

We claim:

1. A process for the preparation of a 2(5H)-furanone of the formula

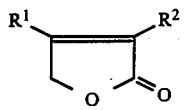 (I)

where $R^1$ and $R^2$ are each hydrogen, $C_1$-$C_6$-alkyl, $C_5$- or $C_6$-cycloalkyl, $C_7$-$C_{12}$-aralkyl or aryl, which comprises:

heating a 3-formyl-carboxylate or 3-formylcarboxylic acid of the formula

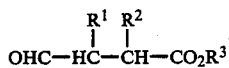 (II)

where $R^3$ is hydrogen, $C_1$-$C_{12}$-alkyl, $C_5$- or $C_6$-cycloalkyl, $C_7$-$C_{12}$-aralkyl or aryl, to 100°–450° C. in the presence of an acidic catalyst and in an otherwise inert liquid or gas phase reaction medium.

2. A process as claimed in claim 1, wherein the acidic catalyst used is an oxide of boron, or aluminum, of silicon, of phosphorus or of a metal of subgroups IV to VI of the Periodic Table.

3. A process as claimed in claim 1, wherein the acidic catalyst used is silica, aluminum trioxide, boron trioxide, titanium dioxide, vanadium pentoxide, chromium trioxide or a mixture of these compounds.

4. A process as claimed in claim 1, wherein the acidic catalyst used is natural or synthetic zeolite.

5. A process as claimed in claim 4, wherein an X, Y or pentasil zeolite is used.

6. A process as claimed in claim 1, wherein $R^1$ and $R^2$ are each $C_1$-$C_6$-alkyl and $R^3$ is $C_1$-$C_{12}$-alkyl.

7. A process as claimed in claim 1, wherein a 3-formylcarboxylate or 3-formylcarboxylic acid is heated to 200°–350° C.

8. A process as claimed in claim 1, wherein the lactonization is carried out in the presence of water or a $C_1$-$C_4$-alcohol or mixtures thereof.

9. A process as claimed in claim 1, wherein the heating step is carried out in the liquid phase in the presence of a suspended fixed-bed catalyst or of a homogeneously dissolved catalyst.

10. A process as claimed in claim 9, wherein a suspended fixed-bed catalyst is used in an amount of 0.5 to 20% by weight, based on the starting material II.

11. A process as claimed in claim 9, wherein a homogeneously dissolved catalyst is used in an amount of from 0.002 to 0.25 mole per mole of the starting material II.

12. A process as claimed in claim 1, wherein the heating step is carried out in the gas phase over a fixed-bed catalyst or with a fluidized catalyst.

13. A process as claimed in claim 12, wherein the space velocity is adjusted to from 0.1 to 10 grams of starting material II per gram of catalyst per hour.

14. A process as claimed in claim 12, wherein the space velocity is adjusted to from 0.1 to 5 grams of starting material II per gram of catalyst per hour.